United States Patent [19]
Fischer et al.

[11] Patent Number: 6,092,252
[45] Date of Patent: Jul. 25, 2000

[54] MOTOR DRIVEN TOOTHBRUSH, IN PARTICULAR AN ELECTRIC TOOTHBRUSH

[75] Inventors: Franz Fischer; Philipp Pfenniger, both of Triengen, Switzerland

[73] Assignee: Trisa Bürstenfabrik AG Triengen, Triengen, Switzerland

[21] Appl. No.: 09/147,828

[22] PCT Filed: Nov. 28, 1997

[86] PCT No.: PCT/CH97/00449

§ 371 Date: Mar. 16, 1999

§ 102(e) Date: Mar. 16, 1999

[87] PCT Pub. No.: WO99/03372

PCT Pub. Date: Jan. 28, 1997

[30] Foreign Application Priority Data

Jul. 16, 1997 [CH] Switzerland .................. 1745/97

[51] Int. Cl.[7] .................................................. A61C 17/34
[52] U.S. Cl. .................................................. 15/22.1; 15/28
[58] Field of Search .................. 15/22.1, 23, 24, 15/28, 29

[56] References Cited

U.S. PATENT DOCUMENTS

| | | | |
|---|---|---|---|
| 1,822,631 | 9/1931 | Roig ............................................ | 15/23 |
| 2,911,660 | 11/1959 | Klemas et al. .............................. | 15/28 |
| 4,149,291 | 4/1979 | Stoltz . | |
| 5,173,983 | 12/1992 | Le ................................................ | 15/28 |
| 5,404,608 | 4/1995 | Hommann ................................... | 15/28 |
| 5,423,102 | 6/1995 | Madison ..................................... | 15/28 |
| 5,467,494 | 11/1995 | Muller et al. . | |
| 5,901,397 | 5/1999 | Hafele et al. ............................ | 15/22.1 |

FOREIGN PATENT DOCUMENTS

| | | |
|---|---|---|
| 510940 | 10/1992 | European Pat. Off. . |
| 2756166 | 6/1979 | Germany ................................ 15/22.1 |
| 4228859A1 | 3/1994 | Germany . |
| 29520230 | 3/1996 | Germany . |
| 6-237821 | 8/1994 | Japan ...................................... 15/22.1 |
| 2172196 | 9/1986 | United Kingdom . |
| 2250428 | 6/1992 | United Kingdom . |
| 9210979 | 7/1992 | WIPO . |

*Primary Examiner*—Terrence R. Till
*Attorney, Agent, or Firm*—Low and Low

[57] ABSTRACT

A motor-driven toothbrush including a brush head disposed at an angle to the brush handle wherein the brush head partakes of rotary or arcuate motion, wherein the handle includes a flexible or articulated section permitting the brush head and an end portion of the handle to deflect with respect to the remainder of the handle as the brush head engages the teeth. The elastic section may be a flexible portion or may be a bellows-like member. The drive for the brush head extends through the elastic section and to the brush head. The flexible section permits the brush head to tilt angularly through an angle either greater or less than 90 degrees with respect to the axis of the brush handle. The brush head is attachable to a separate handle having a drive device.

16 Claims, 2 Drawing Sheets

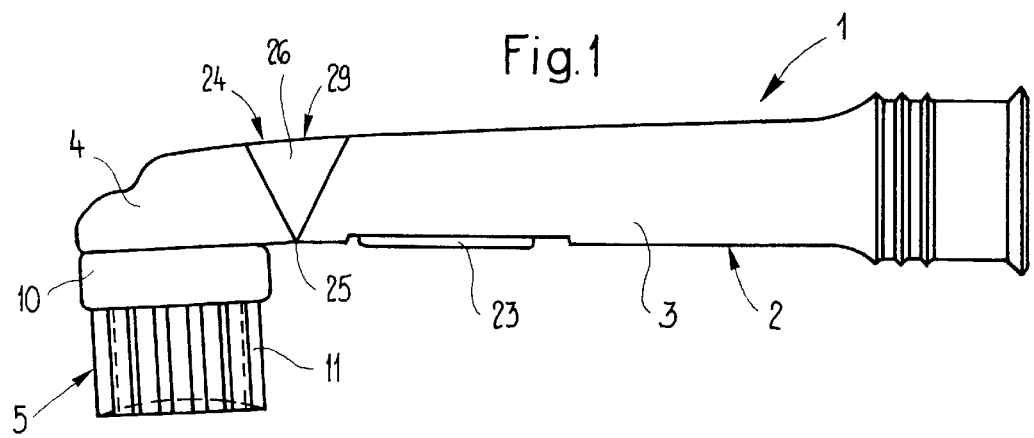
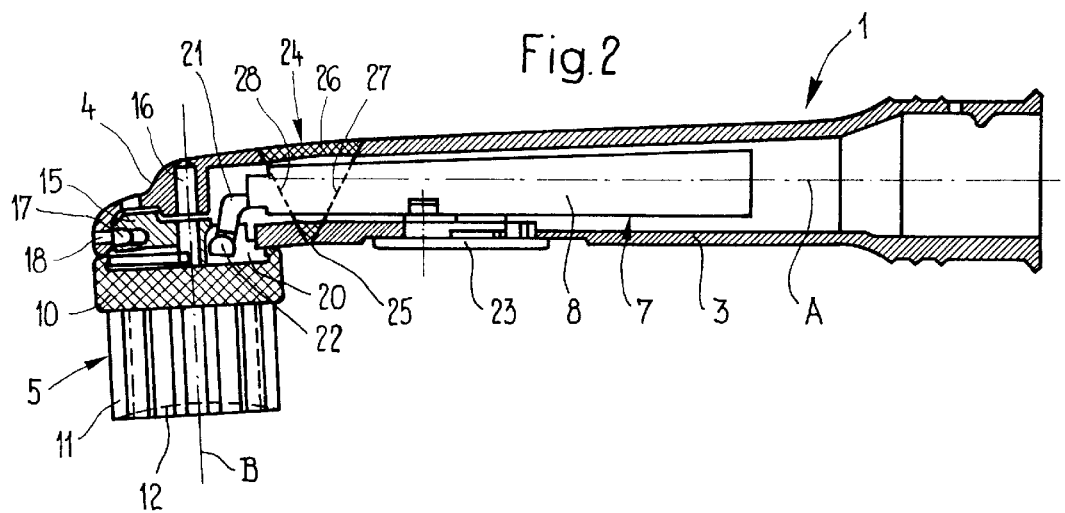
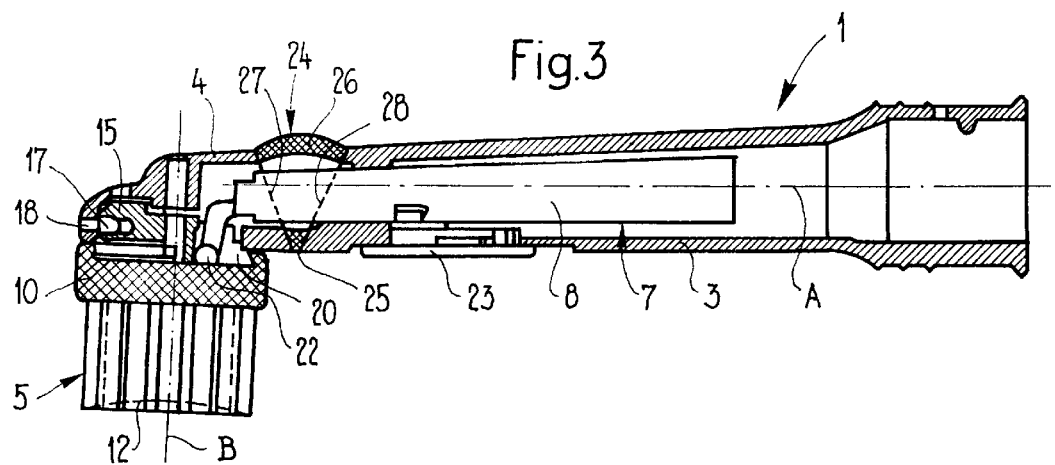

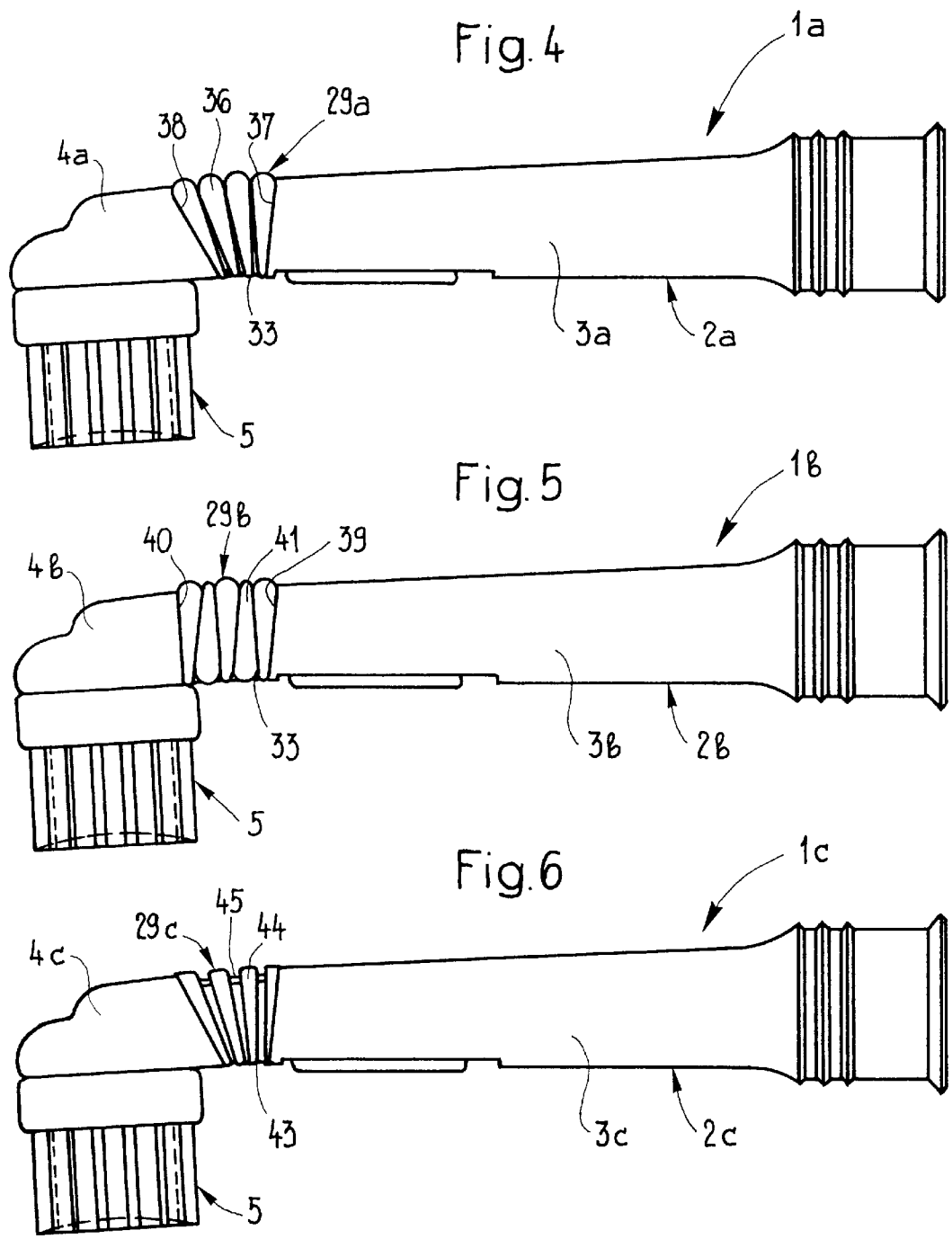

MOTOR DRIVEN TOOTHBRUSH, IN PARTICULAR AN ELECTRIC TOOTHBRUSH

BACKGROUND OF THE INVENTION

The invention relates to a motor-driven toothbrush, in particular an electric toothbrush, as one wherein the brush head partakes of an arcuate rotary-like motion, with the brush head angled to the normal axis of the elongated housing or handle to which it is connected.

A toothbrush of this type is known, for example, from DE-U-295 20 230.0. In the case of this toothbrush, a housing head part, which receives a rotatable bristle carrier, is fixedly connected to a housing part which receives a drive shaft arranged at right angles to the axis of rotation of the bristle carrier.

BRIEF SUMMARY OF THE INVENTION

The object of the present invention is to provide a toothbrush of the type mentioned in the introduction by means of which a better cleaning action can be achieved.

This object is achieved according to the invention by a toothbrush having the features of a brush head which is flexible and tiltable with respect to the axis of the toothbrush housing or handle adjacent the brush head.

Since the housing has a flexing zone and is subdivided by the latter into two housing parts, which can be deflected elastically with respect to one another, with the result that, with forces acting in the direction of the brushing surface, the brush head, which remains in a drive connection, can be forced back or pivoted elastically, use of the toothbrush results in better abutment of the cleaning-action, brushing surface and in an optimum contact pressure.

Preferred developments of the toothbrush are seen in the attached drawings. The invention embraces more than one embodiment as seen in the drawings and described hereinafter.

BRIEF DESCRIPTION OF THE DRAWINGS

An exemplary embodiment of the toothbrush according to the invention is described in more detail hereinbelow and is illustrated in the drawing, in which, purely schematically:

FIG. 1 shows a view of a first exemplary embodiment of a plug-on part of an electric toothbrush;

FIG. 2 shows the longitudinal section of the plug-on part according to FIG. 1 in a normal position;

FIG. 3 shows the longitudinal section of the plug-on part according to FIG. 1 in a deflected position;

FIG. 4 shows a view of a second exemplary embodiment of a plug-on part of an electric toothbrush in the normal position, which corresponds to FIG. 2;

FIG. 5 shows a view of a third exemplary embodiment of a plug-on part of an electric toothbrush in the normal position, which corresponds to FIG. 2; and FIG. 6 shows a view of a fourth exemplary embodiment of a plug-on part of an electric toothbrush in the normal position, which corresponds to FIG. 2.

DETAILED DESCRIPTION OF THE INVENTION

According to FIGS. 1 to 3, a plug-on part 1 for an electric toothbrush has a housing 2 which comprises a rear housing part 3, which can be plugged onto a handle part (not illustrated in the drawing), and a front housing part 4. A brush head 5 is mounted in the front housing part 4 in a rotatable manner, said brush head being driven by an electric motor (not illustrated in the drawing) by means of a transmission device 7, which is accommodated in a cavity 6 of the housing 2 and of which only part can be seen in FIGS. 2 and 3. The brush head 5 is imparted an alternating rotary movement or rotary oscillation, it being possible for the angle-of-rotation range to be adjusted. Such a toothbrush and such a transmission device form the subject matter of DE-U-295 20 230.0; the transmission device 7 is thus not itself described in detail hereinbelow. A drive shaft of the transmission device 7 is designated by 8, and the drive axis by A, in FIGS. 2 and 3. The brush-head axis is provided with the designation B.

The brush head 5 has a bristle carrier 10 with projecting bristles 11. The free ends of the bristles 11 form a brushing surface 12. As an example, a concave brushing surface 12 which is concentric to the brushhead axis B is illustrated.

As can be seen from FIGS. 2 and 3, the bristle carrier 10 is connected in the manner of a snap-action connection to a rotary plate 15, which is mounted in the housing part 4 in a rotatable manner, and can be removed from said rotary plate for the purpose of exchanging the brush head 5. The rotary plate 15, with the brush head 5, can be pivoted in both directions of rotation about an axial pin 16 which is provided in the housing part 4 and is coaxial with the brush-head axis B. The rotary plate 15 is secured axially in the housing part 4 by means of a securing pin 18 which projects into a circle-segment-type recess 17 in the rotary plate 15 and is arranged radially with respect to the brush-head axis B in the housing part 4.

The alternating rotary movement is transmitted from the drive shaft 8 to the rotary plate 15 and to the brush head 5, which is connected to said rotary plate, in the manner which is already known from DE-U-295 20 230.0, namely by means of a protrusion 21 which is assigned to the drive shaft 8 and projects into a radial recess 20 in the rotary plate 15. In this case, the protrusion 21 is provided, in the contact region with the recess 20, with a spherical part 22. It is also possible, in the case of this embodiment of the toothbrush illustrated in FIGS. 1 to 3, for the angle range of the rotary pivoting of the rotary plate 15 and of the brush head 5 to be adjusted by means of an axial displacement of the drive shaft 8, which is provided with the protrusion 21. The displacement of the drive shaft 8, and thus the radial adjustment of the protrusion 21 in the recess 20, for the purpose of angle-range adjustment takes place by the action of switching over a slide 23 which can be adjusted into preferably two different switching positions.

According to the intention, a flexing zone 29. is located between the rear housing part 3 and the front housing part 4, which is provided with the brush head, with the result that during use of the toothbrush, with forces acting in the direction of the brushing surface 12, the housing part 4, with the brush head 5, can be forced back elastically out of the normal position, which is shown in FIG. 2, into a deflected position. In the case of the exemplary embodiment illustrated in FIGS. 1 to 3, the two housing parts 3, 4, which are produced from plastic, are separate from one another and connected to one another merely by means of an articulated connection 24. The articulated connection 24 comprises a thin plastic hinge 25 (film hinge), which forms the pivot axis of the housing part 4, and an articulation sleeve 26. The hinge 25 is arranged at right angles to a plane defined by the brush-head axis B and the drive axis A, which at the same time forms the longitudinal axis of the housing part 3; the pivot axis thus runs perpendicularly with respect to the plane of the drawing.

The articulation sleeve 26, made of an elastomeric material, is installed between the two housing parts 3, 4 or between the mutually facing end surfaces 27, 28 of the same—such that it tapers toward the hinge 25 in the form of a wedge.

In the case of the preferred embodiment illustrated, the front housing part 4, which is provided with the brush head 5, can be forced back or pivoted with respect to the rear housing part 3, in the clockwise direction according to FIG. 2, approximately by 6° about the pivot axis defined by the hinge 25. In this case, the elastomeric articulation sleeve 26 is compressed, the wedge-shape space between the head part 4 and the housing part 3 is reduced, and the elastomeric material bulges some way towards outward on the side remote from the hinge 25 (FIG. 3). As soon as the action of force on the brush head 5 is eliminated, the head part 4, with the brush head 5, returns, under the action of the elastomeric articulation sleeve 26 being relieved of pressure, into the neutral position, which is illustrated in FIG. 2. However, the flexing zone could be designed such that pivoting of the housing part 4, provided with the brush head 5, in the angle range of up to 90° would be possible.

In the case of the embodiment which is illustrated in FIGS. 2 and 3, the protrusion 21 in the normal position, according to FIG. 2, projects into the recess 20 of the rotary plate 15 with play, i.e. not quite as far as the bristle carrier 10; in the deflected position, which is shown in FIG. 3, the protrusion 21 is located in the immediately vicinity of the bristle carrier 10. In both end positions of the housing part 4, engagement of the protrusion 21 in the recess 20 is ensured. In each pivot position of the housing part 4, the spherical part 22 of the protrusion 21 permits satisfactory transmission of movement to the rotary plate 15 and friction-free pivoting of the housing part 4.

If the brush head 5 in operation is forced back out of the normal position by the forces acting in the direction of the brushing surface 12, then the position of the protrusion 21 in the radial recess 20 changes, i.e. the distance between the protrusion 21 and the axial pin 16, which defines the axis of rotation B of the brush head 5, is reduced. This results in the angle of rotation of the brush head 5 being reduced Without there having to be a change in the angle of rotation from the outside. In other words, the angle of rotation of the brush head 5 decreases as the compressive forces acting on the brush head 5 increase.

However, it would also be possible for the drive shaft 8 of the transmission device 7 to be designed such that it can go along with the deflection of the housing part 4 and of the rotary plate 15, mounted in said housing part, so that, when the housing part 4 pivots, the protrusion 21 remains satisfactorily. in engagement with the recess 20. For this purpose, the drive shaft may be configured, for example, as a flexible shaft or may be provided with a universal joint.

The elastic deflectability of the housing part 4, which receives the brush head 5, achieves, during use of the toothbrush, better abutment of the cleaning-action, brushing surface 12 and an optimum contact pressure.

In the case of the exemplary embodiment illustrated, the angle between the brush-head axis B and the drive axis A before pivoting, i.e. in the neutral position, is somewhat smaller than 90°, i.e. the brush head 5 is inclined some way rearward. In the position with maximum deflection, this angle is somewhat greater than 90°; i.e. the brush head 5 is inclined some way forward. However, it would also be possible to aim for other angle relationships of the two axes in the end positions.

In the case of the embodiment which is illustrated in FIGS. 1 to 3, the pivot axis or the hinge 25 is located on the bottom side of the housing 2 and the elastomeric articulation sleeve 26 is subjected to compressive loading when the housing part 4 is forced back. However, it would also be possible for the pivot axis or the hinge 25 to be placed on the top side of the housing 2, with the result that, instead of being subjected to compressive loading, the elastomeric articulation sleeve would be subjected to tensile loading if the housing part 4 were pivoted.

The plug-on part 1 may be produced, for example, by two-component injection molding.

FIG. 4 shows a second exemplary embodiment of a plug-on part 1a for an electric toothbrush. In the case of this exemplary embodiment, the two housing parts 3a, 4a are connected to one another preferably via narrow, flexible webs (which cannot be seen in FIG. 4). While the two housing parts 3a, 4a and the housing region 33, which is formed by the webs, are produced from the same material, a sleeve-like bellows 36 which is made of different, elastomeric material is installed between mutually facing end surfaces 37, 38 of the two housing parts 3a, 4a, said bellows, together with the housing region 33, forming the flexing zone 29a. When the housing part 4a, which is provided with the brush head 5, is forced back, the bellows 36 is subjected to compressive loading.

It is also the case with the third embodiment, which is illustrated in FIG. 5, of a plug-on part 1b that the housing 2b has an elastically flexible housing region 33 which connects the two housing parts 3b, 4b and is preferably formed by narrow webs (which cannot be seen). A bellows 41, which forms the flexing zone 29b together with the housing region 33, is installed between end surfaces 39, 40 of the two housing parts 3b, 4b and is made of an elastomeric material, which is different from the material of the two housing parts 3b, 4b and the webs, is subjected both to compressive loading and to tensile loading when the housing part 4b, which is provided with the brush head 5, is forced back.

The plug-on parts 1a, 1b are also suitable for production by two-component injection molding.

A further embodiment of a plug-on part 1c according to FIG. 6 constitutes a single-component embodiment; the two housing parts 3c, 4c as well as the entire housing wall, and the elastically deformable housing region 43 in the flexing zone 29c, is are produced from the same material and, again, preferably comprises the narrow webs (which cannot be seen in FIG. 6), connecting the two housing parts 3c, 4c, and additionally a sleeve-like part 44. The elastically deformable part 44, which assumes the function of the bellows 36, 41 according to FIGS. 4 and 5, may have a plurality of through-passages 45 for the purpose of increasing the elasticity.

With all of the embodiments described above, it would also be possible for the flexing zone 29 or 29a or 29b or 29c to be arranged further toward the rear in the direction of the handle.

The flexing zone may be configured such that, in addition to that housing part which bears the brush head 5 being pivoted in the plane defined by the brush-head head axis B and the longitudinal axis of the plug-on part, additional lateral pivoting of the same may also take place. This can be made possible, for example, by those embodiments of the flexing zone which are illustrated in FIGS. 4 to 6. However, other configurations with elastic rings or folds would also be conceivable.

The deflectability according to the invention of that housing part which receives the brush head could, of course, also be used for brush heads which, rather than being driven in an alternating manner, are driven in one direction of rotation.

The invention claimed is:

1. A motor-driven toothbrush, in particular an electric toothbrush, comprising:

an elongate housing (2, 2a, 2b, 2c) which has a cavity (6) on the inside, a brush head (5) mounted to the housing (2, 2a, 2b, 2c) in a rotatable manner, said brush head having a bristle carrier (10) with projecting bristles (11), wherein the bristle ends form a brushing surface (12), and wherein the axis of rotation (B) of the brush head (5) is arranged at an angle to the longitudinal axis (A) of the housing (2, 2a, 2b, 2c), a transmission device (7) in the cavity of the housing (2, 2a, 2b, 2c) for coupling to a drive whereby the brush head (5) can be driven in a rotatable manner, wherein the housing (2, 2a, 2b, 2c) has a flexing zone (29, 29a, 29b, 29c) subdividing the housing into two housing parts (3, 3a, 3b, 3c; 4, 4a, 4b, 4c) which can be deflected elastically relative to one another such that with forces acting in the direction of the brushing surface (12), the brush head (5) can be forced back or pivoted elastically in a plane defined by the axis of rotation (B) of the brush head and the longitudinal axis (A) of the housing (2, 2a, 2b, 2c), wherein further the housing (2, 2a, 2b, 2c) is attachable to a separate handle part which is provided with the drive for coupling to the said transmission device (7), and, wherein the transmission device (7) includes structure for maintaining a drive connection to the brush head (5) even when the housing parts (3, 3a, 3b, 3c; 4, 4a, 4b, 4c) are deflected relative to one another.

2. The toothbrush as claimed in claim 1, wherein the flexing zone (29a or 29b or 29c) comprises an elastically deformable housing region (33 or 43) which connects the two housing parts (3a, 3b, 3c; 4a, 4b, 4c) to one another.

3. The toothbrush as claimed in claim 2, wherein the elastically deformable housing region (33 or 43) comprises narrow webs which connect the two housing parts (3a, 4a or 3b, 4b or 3c, 4c).

4. The toothbrush as claimed in claim 3, wherein, together with the elastically deformable housing region (33 or 43), a sleeve-like bellows (36 or 41), which is installed between mutually facing end surfaces (37, 38 or 39, 40) of the two housing parts (3a, 4a or 3b, 4b), forms the flexing zone (29a or 29b).

5. The toothbrush as claimed in claim 3, wherein the elastically deformable housing region (43) is produced from the same material as the two housing parts (3c, 4c) and has a sleeve-like part (44) which is preferable provided with through-passages for the purpose of increasing the elasticity.

6. The toothbrush as claimed in claim 2 wherein, together with the elastically deformable housing region (33 or 43), a sleeve-like bellows (36 or 41), which is installed between mutually facing and surfaces (37, 38 or 39, 40) of the two housing parts (3a, 4a or 3b, 4b), forms the flexing zone (29a or 29b).

7. The toothbrush as claimed in claim 2, wherein the elastically deformable housing region (43) is produced from the same material as the two housing parts (3c, 4c) and has a sleeve-like part (44) which is preferably provided with through-passages for the purpose of increasing the elasticity.

8. The toothbrush as claimed in claim 1, wherein the flexing zone (29) comprises an articulated connection (24) between the two housing parts (3, 4).

9. The toothbrush as claimed in claim 8, wherein the articulated connection (24) comprises a hinge (25), which forms a pivot axis arranged at right angles to the plane defined by the axis of rotation (B) of the brush head and the longitudinal axis (A) of the housing (2), and an elastomeric articulation sleeve (26) between the two housing parts (3, 4).

10. The toothbrush as claimed in claim 9, wherein the elastomeric articulation sleeve (26) is installed between mutually facing end surfaces (27, 28) of the two housing parts (3, 4) in the form of a wedge which tapers toward the hinge (25).

11. The toothbrush as claimed in claim 1 having a drive shaft (8) which is arranged in the cavity (6) of the housing (2, 2a, 2b, 2c) and forms part of the transmission device (7), wherein the drive shaft (8) is designed as a flexible shaft.

12. The toothbrush as claimed in claim 1 wherein that part of the transmission device (7) which is assigned to the deflectable housing part (4, 4a, 4b, 4c) is connected via a universal joint to that part of the transmission device (7) in the other housing part (3, 3a, 3b, 3c).

13. The toothbrushes claimed in one of claim 1 wherein the deflection of the housing part (4, 4a, 4b, 4c) and the change in the angle between the axis of rotation (B) of the brush head and the longitudinal axis (A) takes place in the angle range of from 0° to 90°.

14. The toothbrush as claimed in claim 13 wherein the angle is approximately 6°.

15. The toothbrush as claimed in claim 1, wherein the angle between the axis of rotation (B) of the brush head and the longitudinal axis (A) is somewhat smaller than a right angle in a normal position and somewhat greater than a right angle in a position of maximum deflection, i.e. the brush head (5) is inclined rearward in the normal position and forward in the deflected position.

16. The toothbrush as claimed in claim 1 having a brush head (5) which executes an alternating rotary movement, wherein the transmission device (7) has structure whereby when the brush head (5) is forced back, as a result of forces acting in the direction of the brushing surface (12), the angle of alternating rotation of said brush head decreases.

* * * * *